(12) United States Patent
Johansson et al.

(10) Patent No.: US 6,327,502 B1
(45) Date of Patent: Dec. 4, 2001

(54) IMPLANTABLE STIMULATOR HOUSING WITH ELECTRODE CONNECTOR

(75) Inventors: Göran Johansson, Södertälje; Per Jarl; Rolf Hill, both of Järfälla; David Jergefalk, Stockholm; Gunnar Magnusson, Årsta; Paul Brand, Järfälla; Paul Fröberg, Bromma, all of (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/374,685

(22) Filed: Aug. 16, 1999

(51) Int. Cl.[7] .................................................. A61N 1/375
(52) U.S. Cl. .................................................. 607/36
(58) Field of Search .................................. 607/36, 37, 2; 53/449

(56) References Cited

U.S. PATENT DOCUMENTS

| 4,545,381 | * | 10/1985 | Bournay, Jr. et al. | 607/10 |
|---|---|---|---|---|
| 4,934,366 | * | 6/1990 | Truex et al. | 607/37 |
| 5,324,311 | * | 6/1994 | Acken | 607/37 |
| 5,411,538 | * | 5/1995 | Lin | 607/33 |
| 5,906,634 | * | 5/1999 | Flynn et al. | 607/37 |
| 6,029,089 | * | 2/2000 | Hawkins et al. | 607/37 |

* cited by examiner

Primary Examiner—Kennedy Schaetzle
(74) Attorney, Agent, or Firm—Schiff Hardin & Waite

(57) ABSTRACT

An implantable heart stimulator has a connector for an electrode lead in the form of a self-contained tubular connector, which can be placed as a unit in one-half shell of a stimulator housing, together with a hybrid circuit and a power source. The other half shell of the stimulator housing can then simply be placed over these assembled components and joined thereto by welding, thereby considerably simplifying manufacture and assembly of the stimulator. When an even number of such self-contained connector tubes is employed, the two stimulator housing half shells can be identical.

6 Claims, 2 Drawing Sheets

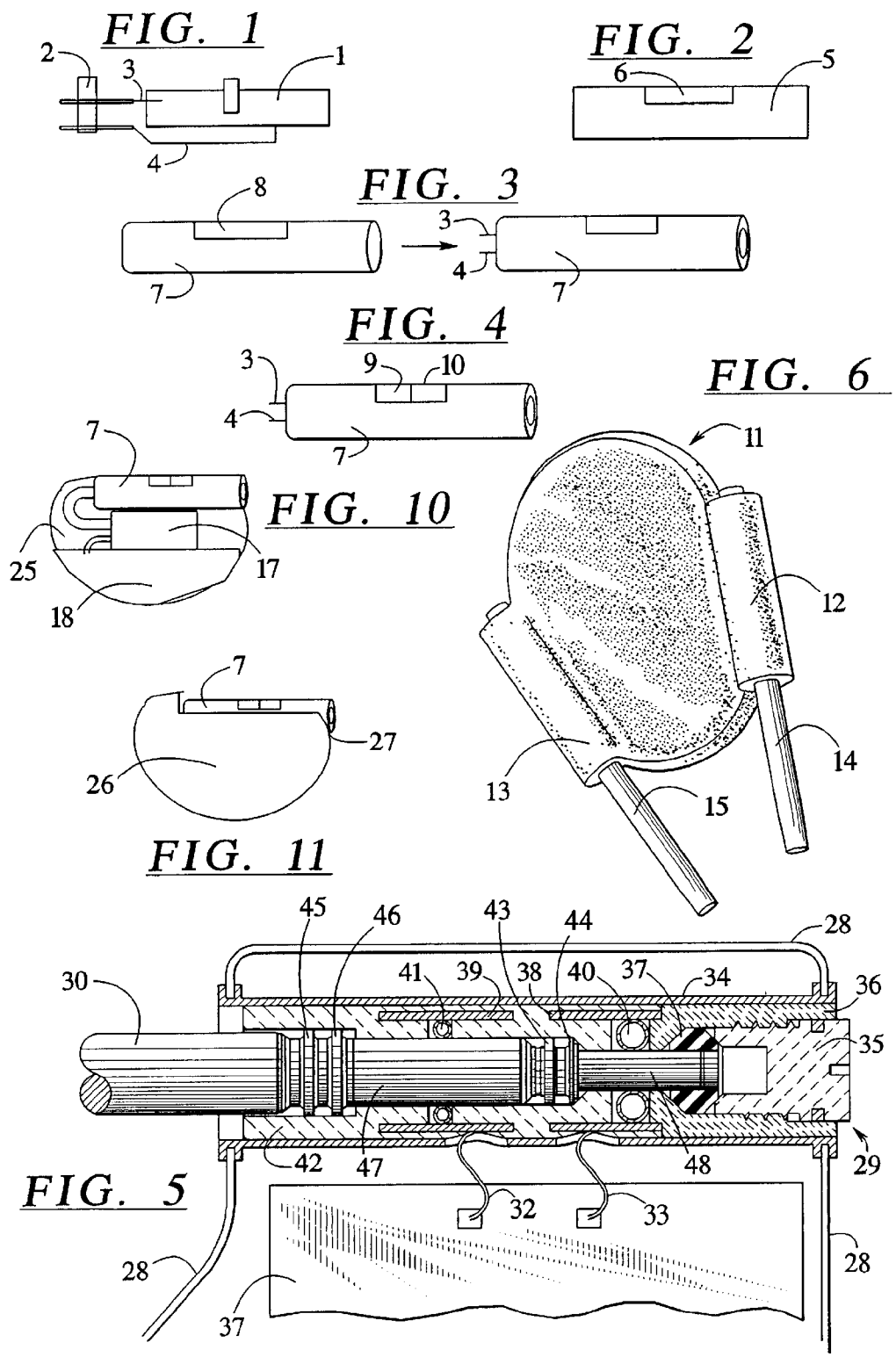

IMPLANTABLE STIMULATOR HOUSING WITH ELECTRODE CONNECTOR

BACKGROUND OF THE INVENTION

1. Field of the Invention

The present invention is directed to a housing for an implantable stimulator, such as an implantable pacemaker, with at least one electrode connector for electrically and mechanically connecting the internal components of the stimulator to an electrode lead.

2. Description of the Prior Art

Implantable stimulators, such as a pacemaker, have a housing (also known as a "can") which contains electronic circuitry and a power source (battery). The stimulator delivers stimulation energy, usually in the form of pulses, in vivo to tissue, such as cardiac tissue, via electrodes which are implanted so as to be in contact with the tissue. One or more electrode leads connect the stimulator to these electrodes. The leads must be mechanically and electrically connected to the housing. A single lead having multiple conductors, leading to respectively different electrodes, can be employed, or multiple leads can be used.

The internal components contained in the housing must be protected against the surrounding environment, especially body fluids, over a relatively long period of time. This requirement imposes high demands on all possible entry paths into the interior of the housing, and particularly on the connections of the leads to the housing. A fluid-type connection must be made between the lead or leads and the housing, but the connection must also afford the possibility to disconnect the stimulator housing from the implanted leads for replacement or servicing of the stimulator.

The connective parts of the stimulator and the leads have been substantially standardized in the pacing field, and generally a relatively deep female socket is used at the stimulator housing, which has a number of contact surfaces, and the lead or leads have a male portion carrying one or more corresponding, peripherally disposed, generally circular, contact surfaces.

Conventionally, the socket portion of the connection is made of a transparent material, usually epoxy resin, which is molded onto the stimulator housing, encompassing contacts which extend outwardly from the housing. The male portion of the lead is normally locked in this socket by set screws, although many other fastening arrangements are known in the art. The positioning and alignment of the different contact surfaces, and the positioning and alignment of the metallic threads for the set screws, prior to the molding of the female portion of the connector is relatively complicated, and there is also an unavoidable delay in the manufacturing process which arises due to the time needed for the epoxy resin to cure.

Moreover, since the connector is disposed at the top of the stimulator housing, the two halves of the housing which are joined together, after the circuit, power source and other components have been mounted therein, must necessarily be non-identical, and are usually mirror-symmetric. This requires that two differently shaped housing halves be manufactured and maintained in inventory.

SUMMARY OF THE INVENTION

It is an object of the present invention to provide a connector for an implantable stimulator device which can be assembled in the stimulator housing without the necessity of a molding procedure, which still providing the necessary fluid-tight mechanical and electrical connection of the electrode lead to the components contained in the stimulator housing.

The above object is achieved in accordance with the principles of the present invention in a connector for an electrode lead which is completely self-contained in an exterior tube, and which can be assembled, as a tubular unit, using two identical housing halves.

The entire assembly is prefabricated with an exterior tube, and it is then only necessary to weld the tube into or onto one of the housing halves. When two such prefabricated tubes are employed, the housing halves can be identical, and there is no need to separately manufacture, and maintain in inventory, two different, mirror-symmetrical, housing halves, as is necessary with conventional molded connections.

The electrical connection between the prefabricated tube and the hybrid substrate in the stimulator housing can be made directly, without the need for feed-throughs, by allowing the edge of the substrate to extend into a slot in the exterior tube, with the substrate being bonded thereto by welding, brazing or gluing. The substrate edge can be provided with contacts which may directly contact the contact pin of the lead, or can produce an electrical contact with the lead via an adapter. The two prefabricated tubes can then be attached to the substrate in advance so as to form a unit, and the entire unit then being placed in one housing half of the stimulator and connected to the battery, after which the other housing half is welded onto the first half. This is a considerable simplification over conventional procedures, wherein thin wires must be bonded to the feed-through block and to the substrate after mounting of the parts.

DESCRIPTION OF THE DRAWINGS

FIG. 1 is a schematic illustration of the internal components of an embodiment of a tube connector for use in the inventive stimulator.

FIG. 2 is a side view of a weld protector for the internal components shown in FIG. 1.

FIG. 3 shows a titanium sleeve at the left part of the figure, which is slid onto the components in FIG. 1 covered by the weld protector of FIG. 2, to result in the assembly shown at the right part of the figure.

FIG. 4 shows the completed tubular connector in accordance with the invention.

FIG. 5 is a side sectional view of a more detailed embodiment of the tubular connector in accordance with the invention.

FIG. 6 shows a stimulator in accordance with the invention with two tubular connectors, in assembled form.

FIG. 10 shows a stimulator employing a tubular connector in accordance with the invention in a further embodiment using a conventionally-shaped housing, with the top housing half removed.

FIG. 11 shows the stimulator of FIG. 10 in completely assembled form.

DESCRIPTION OF THE PREFERRED EMBODIMENTS

Figure 12:
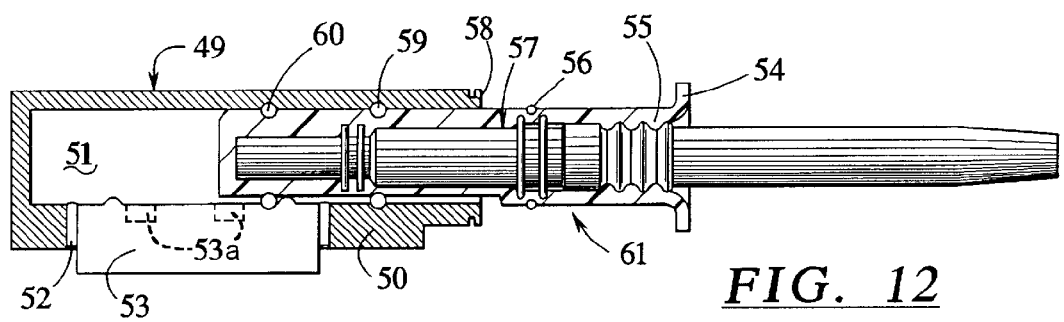
FIG. 12 is a sectional view of a further embodiment of a tubular connector in accordance with the invention.

The internal components of a tubular connector in accordance with the invention are schematically shown in highly simplified form in FIG. 1. These components include an interior tube 1 and a feed-through block 2, with conductors 3 and 4 proceeding through the feed-through block 2 and being electrically and mechanically connected to the interior tube one. FIG. 2 shows a weld protection sleeve 5, having a longitudinal slot 6 therein, in which the components shown in FIG. 1 are contained so as to be protected against subsequent welding. FIG. 3, at the left, shows a titanium sleeve, also having a longitudinal slot 8 therein, which is slid over and welded to the sleeve 5 shown in FIG. 2, resulting in the assembly shown at the right of FIG. 3. The slots 6 and 8 coincide in the assembly shown at the right of FIG. 3.

In the finished tubular connector shown in FIG. 4, a viewing window 9 and a locking device 10 are molded in the coinciding slots 6 and 8 with transparent material. The assembly shown in FIG. 4 is thus a self-contained tubular connector which can be embodied, without further molding procedures, in a stimulator housing. Several examples of the simplified manner of assembling such a stimulator are shown in FIGS. 6 through 11.

Figure 7:
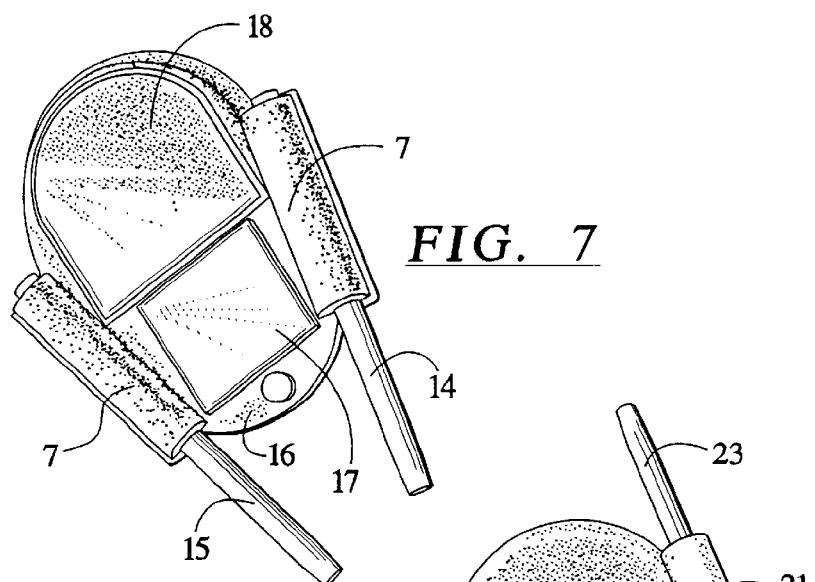
FIG. 7 shows the stimulator of FIG. 6 with the upper half of the stimulator removed.

In the embodiment shown in FIG. 6, a housing 11 has two slightly enlarged regions 12 and 13 at opposite sides thereof, which respectively receive the tube connectors 7, as shown in FIG. 7. The tubular connectors 7 are respectively connected to electrode leads 14 and 15. FIG. 6 shows the housing 11 in completely assembled form, with a top housing half being welded or otherwise joined to a bottom housing half 16, which is visible in FIG. 7 with the top half removed. As can be seen in FIG. 7, before the top housing half is joined to the bottom housing half 16, a hybrid circuit 17 and a battery 18 are positioned, together with the tubular connectors, in the bottom housing half 16. The top housing half then only needs to be fitted over these components, enjoined to the bottom housing half 16. Moreover, as can be seen in FIGS. 6 and 7, the top and bottom housing halves are identical, i.e., they are not mirror-symmetrical as in a conventional pacemaker housing. Therefore, only one housing half shape needs to be manufactured and maintained in inventory, thereby considerably simplifying manufacturing and assembly.

Figure 8:
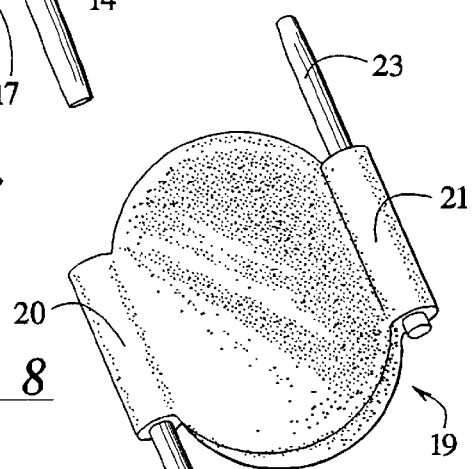
FIG. 8 shows another embodiment of a stimulator in accordance with the invention employing tubular connectors, in assembled form.
Figure 9:
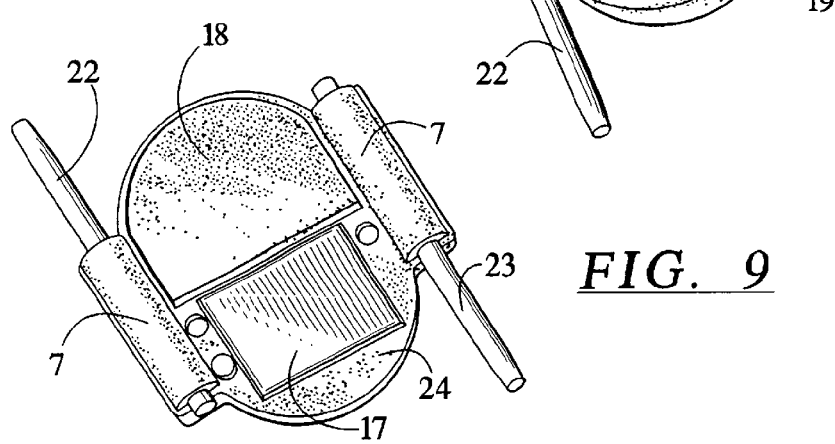
FIG. 9 shows the stimulator of FIG. 8 with the top housing half removed.

Another embodiment wherein identical housing halves can be employed is shown in FIGS. 8 and 9. In this embodiment, the assembled housing 19 shown in FIG. 8 has two enlarged side portions 20 and 21 from which electrode leads 22 and 23 respectively extend. As can be seen in FIG. 9, wherein the top half of the housing has been removed so as to expose the bottom housing half 24, tubular connectors 7 are again mounted at opposite sides of the housing, and a hybrid 17 and a battery 18 are positioned therein. Again, the top housing half only needs to be joined to the bottom housing half with all components mounted therein as shown in FIG. 9.

If more electrodes are needed, it would also be possible to arrange two further electrodes in the embodiment shown in FIGS. 8 and 9 at the unoccupied housing regions, generally forming a square in combination with the illustrated electrode leads.

The embodiment shown in FIGS. 10 and 11 makes use of a conventionally shaped pacemaker housing having mirror-symmetric housing halves, and thus the advantage of being able to manufacture and maintain a single housing half shape does not apply to the embodiment of FIGS. 10 and 11, but the overall assembly using the self-contained connector tube 7 is still applicable. FIG. 10 shows a conventional posterior housing half 25, with the tubular connector 7 and the hybrid 17 and the battery 18 mounted therein, electrically connected by lead wires. FIG. 11 shows the completely assembled stimulator, with the front half 26 of the housing welded in place, not only to the posterior housing half 25, but also to the tubular connector 7, by means of weld seam 27.

FIG. 5 is a sectional view of one embodiment of a tubular connector 29, shown mounted in a housing 28 with a lead 30 inserted therein. The housing 28 contains a hybrid circuit 31, to which the tubular connector 29 is electrically connected by wires 32 and 33, which are appropriately bonded to the hybrid circuit 31, and which proceed through openings in the outer sleeve 34 of the tubular connector 29. As can be seen in FIG. 5, the opposite ends of the outer sleeve 34 of the tubular connector 29 have annular channels therein, so that the tubular connector 29 is held in place by the housing 28.

From one end of the tube 34 (the left side in FIG. 5), a ceramic plug 42 is inserted, in which contact rings 38 and 39 have been molded. The ceramic plug 42 has a central bore therein which is shaped to accommodate the lead 30. The ceramic plug 42 has an annular channel in which a circular spring contact 40 is inserted, in mechanical and electrical contact with the contact 39. The contact 38 projects beyond the inner terminating end of the plug 42, and thus an open annular channel is present at that end of the plug 42, which receives another circular spring contact 40, in electrical and mechanical contact with the contact 38. This open end of the plug 42 is closed by a cylindrical component 36, which is inserted through the other end (the right end in FIG. 5) of the sleeve 34. The plug 36 has a central bore therein, which may be provided with threads. A resilient locking ring 37 is inserted into the bottom of this bore, and the bore is closed by a plug 35 which is screwed into the threads in the bore of the plug 36.

The lead 30 carries four sealing rings 43, 44, 45 and 46. The lead 30 has a first contact surface 47 which, when the lead 30 is inserted in the opening in the tubular connector 29, makes electrical contact with the contact 41, to produce an electrical path to the hybrid circuit 31 via the contact 41, the contact 39 and the wire 32. The lead 30 also has a second contact surface 48 which, when the lead 30 is inserted in the tubular connector 29, makes electrical contact with the contact 40, thereby producing an electrical path to the hybrid circuit 31 via the contact 40, the contact 38 and the wire 33.

Another embodiment is shown in FIG. 12, wherein a substrate 53 of ceramic material is mounted in a slot 52 of an exterior tube 50 of the tubular connector 49. The substrate 53 is for the purpose of making electrical connections to the circuitry within the stimulator housing. The exterior tube 50 has a cylindrical bore 51 therein, which receives an end of an electrode lead 57 in a tubular adapter 61. The tubular adapter 61 has a flanged end 55, one side 54 of which is hinged so as to be openable to allow the lead 57 to be inserted therein, and can be provided with annular ribs so that when it is closed, as shown in FIG. 12, the lead 57 is firmly held therein. The lead 57 has sealing rings and contact surfaces as described in connection with the embodiment of FIG. 5. O-rings 56, 59 and 60 are provided for sealing purposes. Contacts 53a (which are not visible in the sectional plane shown in FIG. 12 and which are therefore schematically indicated by dashed lines) provide an electrical path between the lead 57 and the substrate 53.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for assembling an implantable stimulator comprising the steps of:

providing a hybrid circuit, a power source, and at least one self-contained connector tube, said self-contained connectortube adapted to receive an electrode lead;

providing first and second separate stimulator housing halves, said first and second housing halves being identical;

mounting said at least one self-contained connector tube, said hybrid circuit and said power source in said first stimulator housing half; and closing said first stimulator housing half with said second stimulator housing half and welding said first and second stimulator housing halves together to produce a closed, fluid-tight stimulator housing containing said self-contained connector tube, said hybrid circuit and said power source.

2. A method as claimed in claim 1 wherein the step of providing at least one self-contained connectortube comprises providing an even number of self-contained connector tubes.

3. An implantable heart stimulator comprising:

first and second self-contained connector tubes, each adapted to receive an electrode lead;

a hybrid circuit electrically connected to each of said first and second self-contained connector tubes;

a power source electrically connected to said hybrid circuit; and first and second housing halves joined together to contain said first and second self-contained connector tubes, said hybrid circuit and said power source, said first and second housing halves being identical.

4. An implantable heart stimulator as claimed in claim 3 wherein each of said first and second self-contained connector tubes comprises:

a metallic barrel bonded to one of said first and second housing halves and having a cavity therein containing electrical contacts adapted for electrically contacting contact surfaces of an electrode lead, and a substrate having electrical contacts thereon extending through said barrel and producing an electrical path between an interior of said cavity and said hybrid circuit.

5. An implantable heart stimulator as claimed in claim 4 wherein said cavity of said barrel has an opening at an end thereof and has a sidewall with an opening therein in which said substrate is mounted, and a tubular adapter composed of insulating material inserted and sealingly locked in said cavity, said tubular adapter having an interior end portion adapted to receive and lock said electrode lead therein when said tubular adapter is inserted in said cavity in said barrel.

6. An implantable heart stimulator as claimed in claim 3 wherein each of said first and second self-contained tubular connectors comprises:

a metallic tube bondable to one of said first and second housing halves, said metallic tube being structurally intact along an entire length of said metallic tube, and a ceramic plug contained in said metallic tube having electrical contacts embedded therein adapted to make an electrical connection with an electrode lead inserted into said metallic tube.

* * * * *